United States Patent
Tu

(10) Patent No.: US 6,561,026 B2
(45) Date of Patent: May 13, 2003

(54) HYDROMETER

(76) Inventor: Chih Yao Tu, 3F, No. 241, Sec. 1, Da-An Rd., Taipei City (TW)

( * ) Notice: Subject to any disclaimer, the term of this patent is extended or adjusted under 35 U.S.C. 154(b) by 84 days.

(21) Appl. No.: 09/893,049

(22) Filed: Jun. 26, 2001

(65) Prior Publication Data

US 2002/0194912 A1 Dec. 26, 2002

(51) Int. Cl.$^7$ .................................................. G01N 9/00
(52) U.S. Cl. ........................................................ 73/454
(58) Field of Search ................................ 73/32 R, 451, 73/454

(56) References Cited

U.S. PATENT DOCUMENTS 4,697,454 A * 10/1987 Lu ................................ 73/440
5,631,420 A * 5/1997 Wong ........................... 73/454

* cited by examiner

Primary Examiner—Richard A. Muller
(74) Attorney, Agent, or Firm—Pro-Techtor International Services

(57) ABSTRACT

A hydrometer comprises a transparent container including a top opening, two arcuate dividers extended from both sides of top opening for dividing the interior of container into a measuring chamber and two opposite side channels each having a bottom open end in communication with measuring chamber and a top inlet open to outside, and a pointer pivotably mounted inside measuring chamber and adapted for indicating a specific gravity of liquid (e.g., sea water) contained in measuring chamber A fluid path is formed from top inlet through channel and bottom open end into measuring chamber as container immersed in the liquid to be measured. This can avoid the generation of bubbles. Further, the time(s) of adjustment of the specific gravity of liquid can be precisely determined.

1 Claim, 5 Drawing Sheets

HYDROMETER

FIELD OF THE INVENTION

The present invention relates to hydrometers and more particularly to a hydrometer for measuring a specific gravity of sea water contained in a fish tank.

BACKGROUND OF THE INVENTION

A conventional hydrometer for measuring a specific gravity of sea water contained in a fish tank is shown in FIG. 1. The hydrometer comprises a transparent, thin and flat liquid container 1 open to the top, an axis 2 coupled to the surface of liquid container 1, a pointer 3 having one end pivotably mounted on axis 2, a weight 4 on pointer 3 located between axis 2 and pointed end of pointer 3, and a graduated scale 5 adjacent one side pointed by pointer 3. In use, dip liquid container 1 into sea water to cause water to flow from the top opening into the container 1. This may force pointer 3 to displace for indicating the specific gravity of sea water when the liquid level in liquid container 1 has reached the pointed end of pointer 3. Further, a preparation of the specific gravity of sea water is necessary so as to meet requirements. However, the previous hydrometer suffered from a couple of disadvantages. For example, the times of necessary preparation are unacceptable high. Further, air and liquid may mix to form bubbles as liquid container 1 dipped into sea water since water flows from the top opening into the container. Such bubbles tend to adhere to pointer 3, thus adversely affecting the accuracy of reading of graduated scale 5.

U.S. Pat. No. 5,631,420 to Wong discloses a hydrometer provided with a measuring chamber and a concealed liquid sample intake pipe having a bottom open end and a top open end. By dipping the bottom open end in liquid, the liquid is forced to flow from the bottom open end through the top bottom open end into the inside of measuring chamber to force pointer 3 to displace and to indicate the specific gravity of the liquid. It is advantageous for avoiding the operator's hand from being contaminated. However, above drawbacks such as higher times of preparation and the presence of bubbles still exist. Thus, it is desirable to provide an improved hydrometer in order to overcome the above drawbacks of prior art.

SUMMARY OF THE INVENTION

It is therefore an object of the present invention to provide a hydrometer comprising a transparent container including a top opening, a pair of opposite arcuate dividers extended from both sides of the top opening for dividing an interior space of the container into a measuring chamber and a pair of opposite channels abutted side walls of the container, each channel having a bottom open end in fluid communication with the measuring chamber and a top inlet open to outside, and a pointer pivotably mounted inside the measuring chamber and adapted for indicating a specific gravity of liquid contained in the measuring chamber wherein a fluid path is formed from the top inlet through the channel and the bottom open end into the measuring chamber as the container immersed in the liquid to be measured. In operation, air in measuring chamber is evacuated from top opening gradually as liquid level in measuring chamber rises, thus avoiding the generation of bubbles. Further, operator can visually clearly read the specific gravity of liquid (e.g., sea water). Hence, operator can precisely determine the time(s) of necessary adjustment of the specific gravity of sea water in fish tank for meeting requirements. As a result, time and labor are saved.

The above and other objects, features and advantages of the present invention will become apparent from the following detailed description taken with the accompanying drawings.

DETAILED DESCRIPTION OF THE PREFERRED EMBODIMENTS

Figure 1:
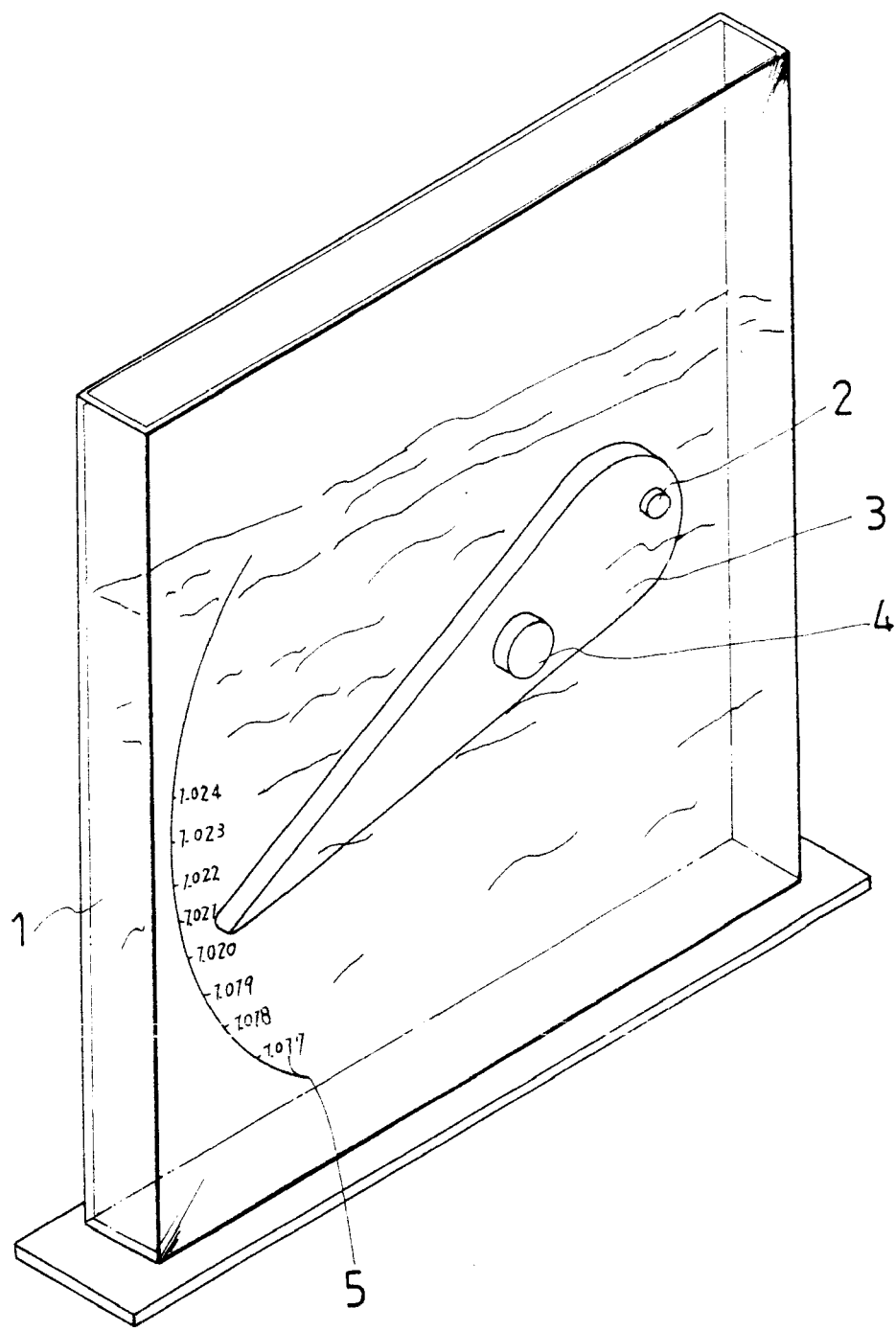
FIG. 1 is a perspective view of a conventional hydrometer.
Figure 2:
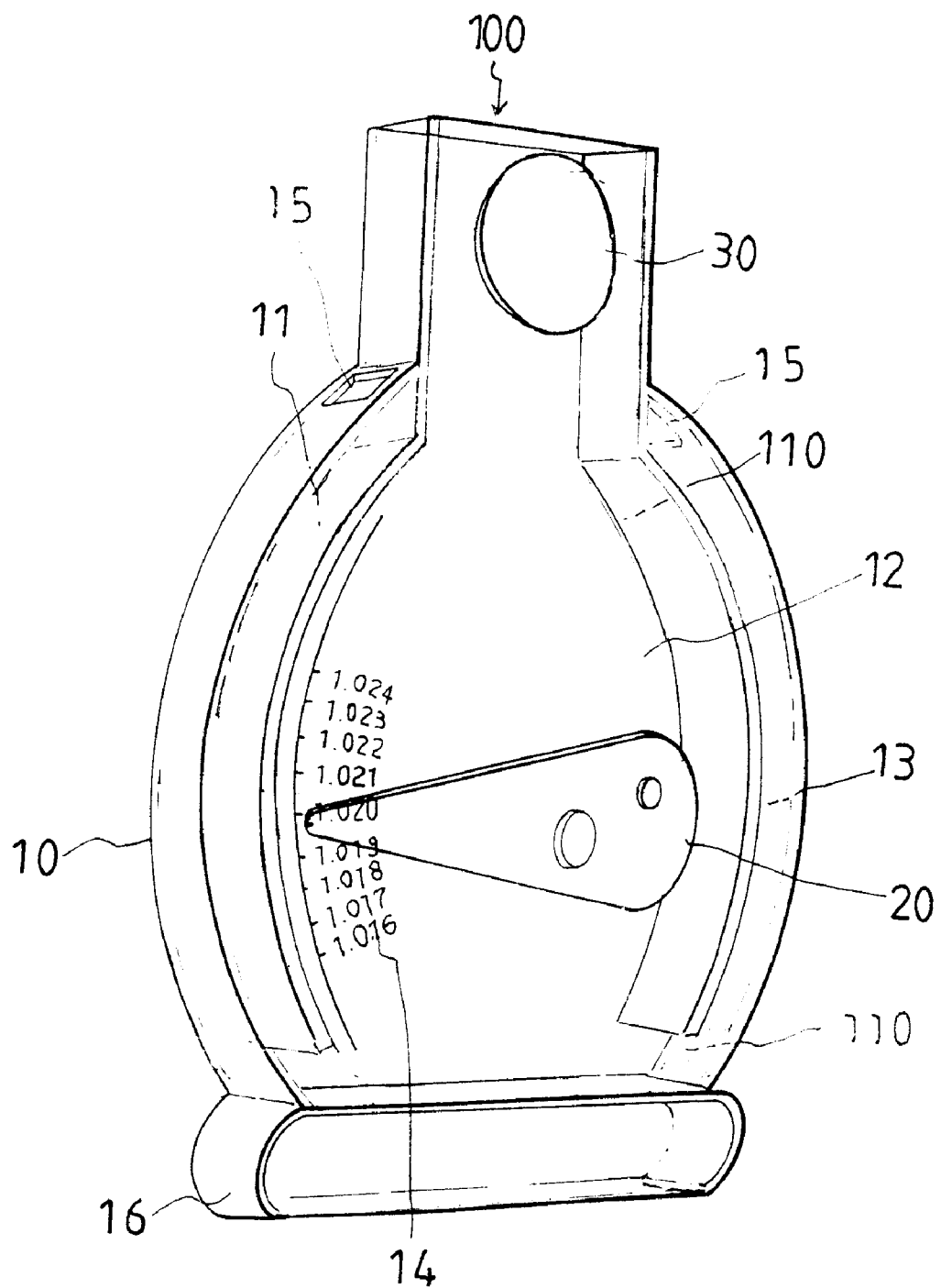
FIG. 2 is a perspective view of a first preferred embodiment of hydrometer according to the invention.
Figure 3:
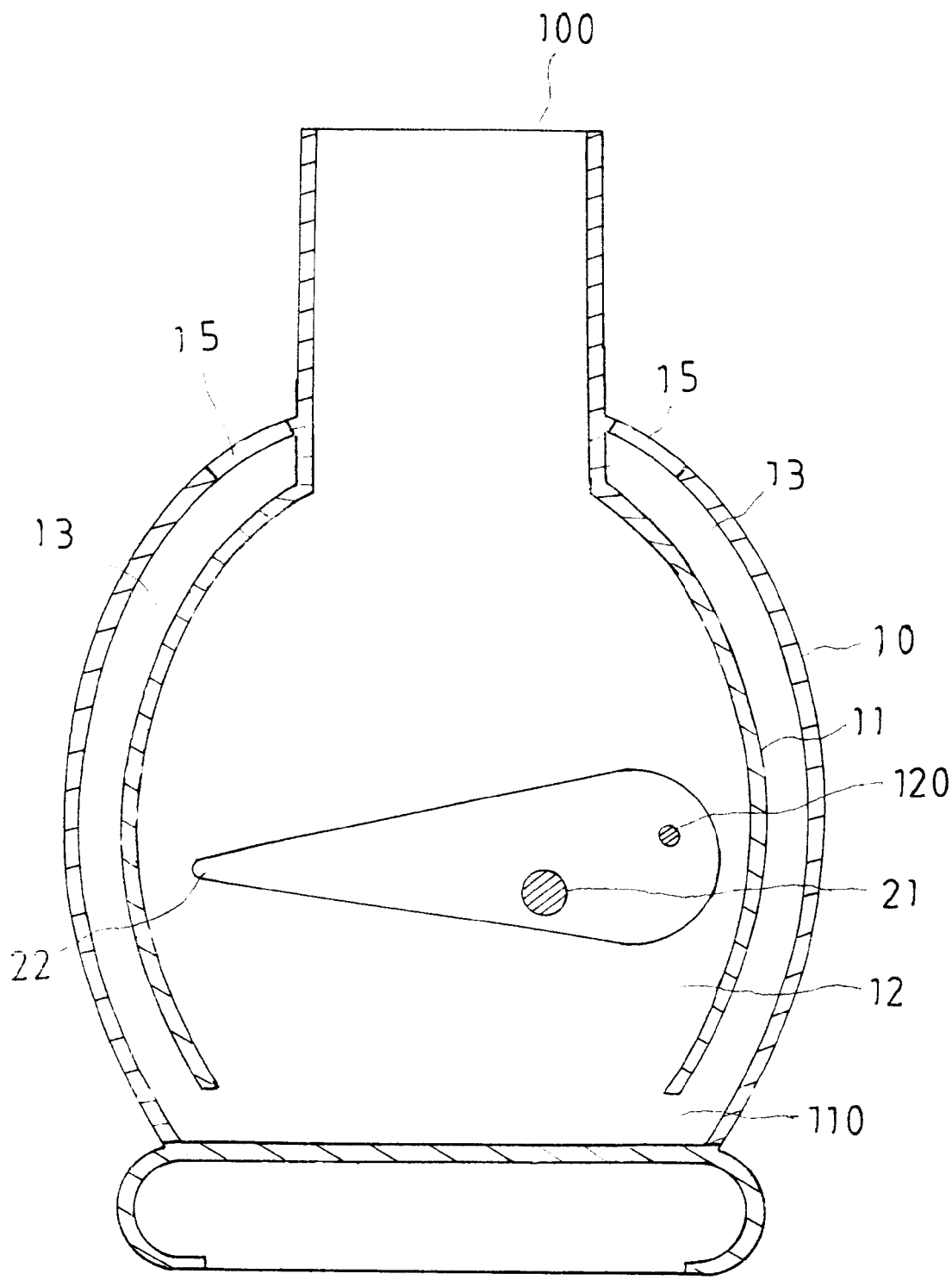
FIG. 3 is a cross-sectional view of FIG. 2.
Figure 4:
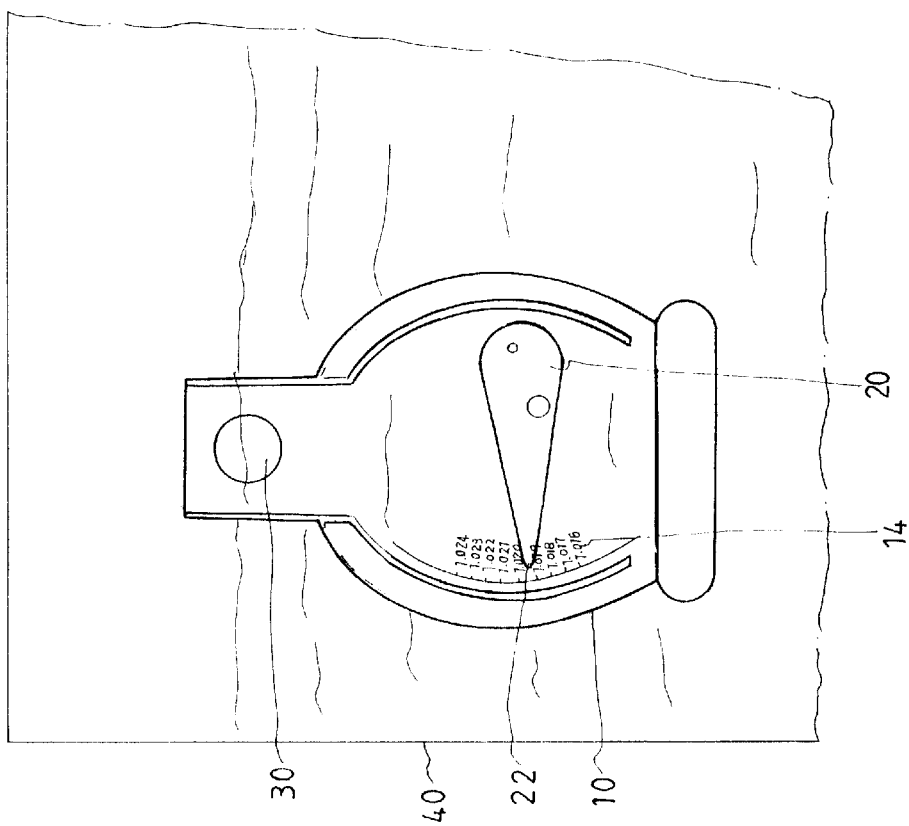
FIG. 4 is an environmental view of the FIG. 2 hydrometer adhered to surface of a fish tank containing sea water.

Referring to FIGS. 2 to 4, there is shown a first preferred embodiment of hydrometer constructed in accordance with the invention comprising a transparent, thin and flat liquid container 10 open to the top 100, a pair of opposite arcuate dividers 11 extended down from both sides of top opening 100 for dividing the interior space of liquid container 10 into a central measuring chamber 12 and a pair of opposite channels 13 abutted the side walls of liquid container 10 wherein channels 13 are in fluid communication with measuring chamber 12 in bottom open ends 110 and with outside in top inlets 15 thereof respectively, an axis 120 coupled to the surface of liquid container 10, a pointer 20 having one end pivotably mounted on axis 120, a weight 21 on pointer 20 located between axis 120 and pointed end of pointer 20, a graduated scale 14 adjacent one channel 13 pointed by pointer 20, and a base 16 The hydrometer further comprises a suction cup 30 coupled to the surface of the container 10 near top opening 100.

In use, immerse liquid container 10 into fish tank 40 to allow sea water to flow from top inlets 15 down through channels 13 and bottom open ends 110 into measuring chamber 12 with suction cup 30 adhered to wall of a fish tank 40. This may force pointer 20 to displace and to indicate the specific gravity of sea water when liquid level in measuring chamber 12 has reached the pointed end of pointer 20. At this time, air in measuring chamber 12 is evacuated from top opening 100 gradually as liquid level in measuring chamber 12 rises, thus avoiding the generation of bubbles. Hence, the hydrometer of the invention can achieve an accurate measurement of specific gravity of sea water. Further, operator can visually read the specific gravity of sea water from graduated scale 14. Hence, operator can precisely determine the time(s) of necessary adjustment of the specific gravity of sea water in fish tank 40 for meeting requirements. As a result, time and labor are saved.

Figure 5:
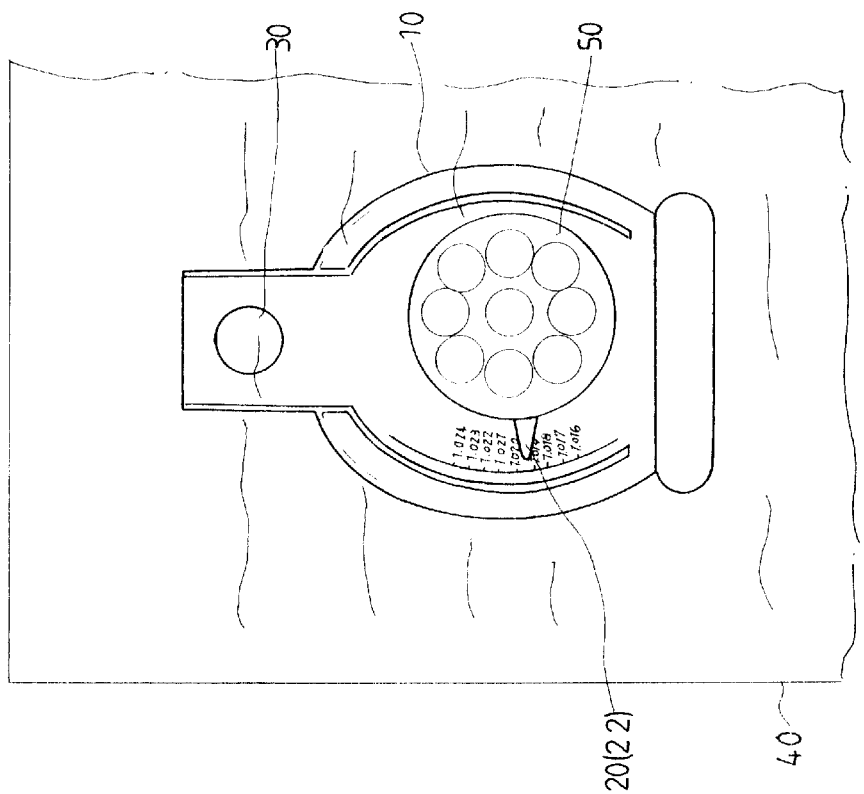
FIG. 5 is an environmental view of a second preferred embodiment of hydrometer according to the invention adhered to surface of a fish tank containing sea water.

Referring to FIG. 5, there is shown a second preferred embodiment of hydrometer according to the invention. The difference between this and first preferred embodiments of hydrometer is that a temperature measurement device 50 is adhered to the surface of liquid container 10. Hence, by using this hydrometer operator may know the temperature of sea water while measuring the specific gravity thereof at the same time.

Figure 6:
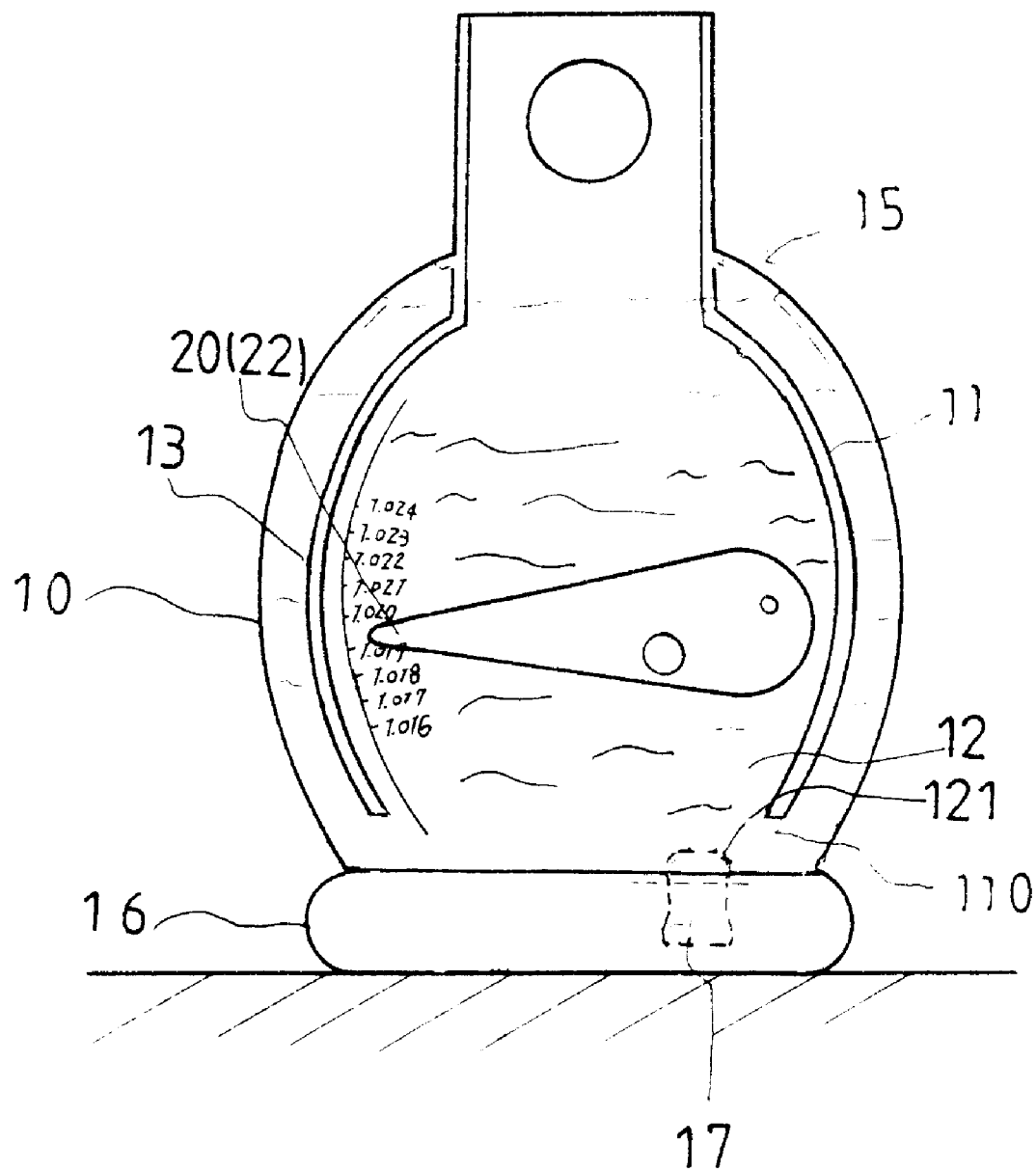
FIG. 6 is a side view of a third preferred embodiment of hydrometer according to the invention.

Referring to FIG. 6, there is shown a third preferred embodiment of hydrometer according to the invention. The differences between this and above two preferred embodiments of hydrometer are as below. There are provided an opening 121 on the bottom of measuring chamber 12 in fluid communication with the inside of base 16 (which is open to outside at its bottom) and a stopper 17 releasably secured in opening 121. This embodiment is particularly suitable for outdoor use. For example, operator may immerse liquid container 10 into fish tank 40 to allow sea water to flow from top inlets 15 into measuring chamber 12. This in turn forces pointer 20 to displace and to indicate the specific gravity of sea water when liquid level in measuring chamber 12 has reached the pointed end of pointer 20. After use, simply remove stopper 17 from opening 121 to drain sea water in measuring chamber 12 through opening 121.

While the invention has been described by means of specific embodiments, numerous modifications and variations could be made thereto by those skilled in the art without departing from the scope and spirit of the invention set forth in the claims.

What is claimed is:

1. A hydrometer comprising a transparent container including a top opening, a pair of opposite arcuate dividers extended from both sides of said top opening for dividing an interior space of said container into a measuring chamber and a pair of opposite channels abutted side walls of said container, each channel having a bottom open end in fluid communication with said measuring chamber and a top inlet open to outside, and a pointer pivotably mounted inside said measuring chamber and adapted for indicating a specific gravity of liquid contained in said measuring chamber wherein a fluid path is formed from said top inlet through said channel and said bottom open end into said measuring chamber as said container immersed in the liquid to be measured.

* * * * *